(12) United States Patent
Storz

(10) Patent No.: US 11,730,560 B2
(45) Date of Patent: Aug. 22, 2023

(54) FAST-ACTION CLAMPING DEVICE WITH LOCKING MECHANISM, AND SURGICAL DEVICE

(71) Applicant: Olaf Storz, Tuttlingen (DE)

(72) Inventor: Olaf Storz, Tuttlingen (DE)

(73) Assignee: STUCKENBROCK MEDIZINTECHNIK GMBH, Tuttlingen (DE)

( * ) Notice: Subject to any disclaimer, the term of this patent is extended or adjusted under 35 U.S.C. 154(b) by 219 days.

(21) Appl. No.: 16/920,540

(22) Filed: Jul. 3, 2020

(65) Prior Publication Data

US 2021/0007823 A1    Jan. 14, 2021

(30) Foreign Application Priority Data

Jul. 12, 2019  (DE) ...................... 10 2019 118 992.6

(51) Int. Cl.
*A61B 90/00* (2016.01)
*A61B 90/14* (2016.01)

(52) U.S. Cl.
CPC .................................. *A61B 90/14* (2016.02)

(58) Field of Classification Search
CPC ......... A61B 90/14; A61B 90/25; A61B 90/35; A61B 90/16; A61B 90/11; A61B 90/17; A61B 90/30; A61B 90/50; A61B 90/57; A61B 2090/571; A61G 13/101; A61G 13/121; A61G 7/1084; A61G 7/072; A61G 7/0506
USPC .............................................................. 70/19
See application file for complete search history.

(56) References Cited

U.S. PATENT DOCUMENTS

| | | | |
|---|---|---|---|
| 2,366,972 A * | 1/1945 | Lawrence | A61G 13/12 5/648 |
| 4,424,724 A * | 1/1984 | Bookwaiter | A61B 17/0293 74/540 |
| 4,964,748 A | 10/1990 | McFadden | |
| 5,560,728 A | 10/1996 | McFadden | |
| 5,564,663 A | 10/1996 | Cook et al. | |
| 6,676,669 B2 | 1/2004 | Charles et al. | |
| 7,093,313 B2 | 8/2006 | Debraal et al. | |
| 7,117,551 B1 | 10/2006 | Dinkler, II et al. | |
| 7,552,492 B2 | 6/2009 | Rolfes et al. | |
| 8,286,283 B2 | 10/2012 | Copeland et al. | |

(Continued)

FOREIGN PATENT DOCUMENTS

| DE | 8802938 | 4/1988 |
|---|---|---|
| DE | 202008014758 U1 | 5/2009 |

(Continued)

OTHER PUBLICATIONS

Search Report for DE 10 2019 118 992.6 dated Apr. 14, 2020.

*Primary Examiner* — Adam Baker
(74) *Attorney, Agent, or Firm* — Aird & McBurney LP

(57) ABSTRACT

The present disclosure relates to a fast-action clamping device includes a handle including rod recesses, a tension rod and a link lever that can apply a fast-action clamping to a portion of an object that can have a rod-shaped from. The device is formed in that sections of an object may be received in the rod recesses and clamped in a clamping position without a clamping position of the link lever, set by a user, being able to pass into a non-clamping position. It also relates to a surgical device which includes such a fast-action clamping device.

12 Claims, 13 Drawing Sheets

(56) References Cited

U.S. PATENT DOCUMENTS

| | | | |
|---|---|---|---|
| 8,683,630 B2 | 4/2014 | Rolfes | |
| 9,107,792 B2 | 8/2015 | Catacchio et al. | |
| 9,681,924 B2 | 6/2017 | Rolfes | |
| 9,730,851 B2 | 8/2017 | Clark et al. | |
| 9,782,317 B2 | 10/2017 | Mount | |
| 9,962,147 B2 | 5/2018 | O'Connell et al. | |
| 10,045,901 B2 | 8/2018 | Catacchio et al. | |
| 2006/0185092 A1 | 8/2006 | McFadden | |
| 2008/0072381 A1* | 3/2008 | Rolfes | A61B 90/14 5/637 |
| 2010/0249780 A1* | 9/2010 | Rolfes | A61B 90/14 606/59 |
| 2012/0238828 A1* | 9/2012 | Fricke | A61B 90/50 600/230 |
| 2017/0245951 A1 | 8/2017 | Crawford et al. | |

FOREIGN PATENT DOCUMENTS

| | | |
|---|---|---|
| DE | 202010010363 U1 | 11/2010 |
| DE | 112007002226 B4 | 4/2017 |
| EP | 0660694 B1 | 11/1997 |
| EP | 0992227 A2 | 4/2000 |
| EP | 2734169 A1 | 5/2014 |
| WO | 2004084751 A2 | 10/2004 |

\* cited by examiner

FAST-ACTION CLAMPING DEVICE WITH LOCKING MECHANISM, AND SURGICAL DEVICE

The present invention relates to a fast-action clamping device according to claim 1 and to a surgical device according to claim 7.

During a series of surgical interventions, it is necessary to hold the patient or parts of the body such as the patient's head in a desired position. In practice, for example head clamps are used for this purpose. They are stationary fixed, e.g. on the operating table, and comprise pins that apply pressure to the bony head from different sides of the head in order to clamp the head between them. Known from practice are fast-action clamping devices for the rapid and simple change of the position of the head clamp relative to the body section on the operating table.

An object of the present invention is to specify a further fast-action clamping device and a further surgical device.

The object of the present invention is achieved by the fast-action clamping device with the features of claim 1 and the surgical device with the features of claim 7.

For this purpose, the present invention proposes a fast-action clamping device.

The fast-action clamping device according to the present invention comprises a handle (alternative terms would be tripod body or base body, which could be used synonymously here), at least a first rod recess and/or a second rod recess. The rod recesses are each designed and/or suitable to receive a section of an object, in particular of a rod or an arm. In this, they may clamp this section in the rod recess. For this purpose, the fast-action clamping device is transferred from a non-clamping position into a clamping position.

Furthermore, the fast-action clamping device according to the present invention comprises a tension rod. This is arranged to exert tension on the first rod recess and/or on the second rod recess. This tension causes the clamping via the fast-action clamping device, as the latter is transferred from the non-clamping position into the clamping position.

In addition, the fast-action clamping device according to the present invention comprises a link lever which is pivotally connected to the handle using a hinge mechanism. Moreover, the link lever is directly or indirectly connected to the tension rod such that during its pivoting, the tension exerted by the tension rod on the first rod recess and/or on the second rod recess is changed.

The link lever comprises or is connected to a locking section, in particular an arch section. The locking section is arranged to interact together with a blocking section, in particular a pawl, in order to disable or prevent automatic transition of the link lever from a position of the link lever set by a user towards the non-clamping position.

Furthermore, the present invention proposes a surgical device for use in a medical treatment. The surgical device comprises at least one fast-action clamping device according to the present invention.

Embodiments according to the present invention may comprise one or several of the aforementioned or the following features in any combination, unless the specific embodiment is recognized as being technically impossible by the person skilled in the art.

In all of the following statements, the use of the expression "may be" or "may have" and so on, is to be understood synonymously with "preferably is" or "preferably has," and so on respectively, and is intended to illustrate an embodiment according to the present invention.

Whenever numerical words are mentioned herein, the person skilled in the art shall recognize or understand them as indications of numerical lower limits. Unless it leads the person skilled in the art to an evident contradiction, the person skilled in the art shall comprehend for example the specification of "one" as encompassing "at least one". This understanding is also equally encompassed by the present invention as the interpretation that a numerical word, for example, "one" may alternatively mean "exactly one", wherever this is evidently technically possible for the person skilled in the art. Both understandings are encompassed by the present invention and apply to all numerical words used herein.

Advantageous developments of the present invention are each subject-matter of the dependent claims and embodiments.

Whenever an embodiment is mentioned herein, it represents an exemplary embodiment according to the present invention.

When it is disclosed herein that the subject-matter according to the present invention comprises one or several features in a certain embodiment, it is also respectively disclosed herein that the subject-matter according to the present invention does, in other embodiments, likewise according to the present invention, explicitly not comprise this or these features, for example, in the sense of a disclaimer.

Therefore, for every embodiment mentioned herein it applies that the converse embodiment, e.g. formulated as negation, is also disclosed.

Embodiments according to the present invention may comprise one or several of the aforementioned and/or of the following stated features in any technically possible combination.

In several embodiments, the locking section preferably comprises a plurality of teeth, arranged in order to be able to interact with a blocking section, in particular a pawl. The teeth may be arranged in a row of teeth adjacent to each other.

In some embodiments, the locking section allows the user to set a clamping position from a plurality of possible clamping positions. For example, the user may set a less strongly jammed clamping position, or one or several more strongly jammed clamping positions. This allows the user to select the desired clamping action at least from a large number of clamping positions. In addition, rods or the like of different widths or diameters may be securely clamped in the rod recesses.

In several embodiments, the locking section, in particular the arch section, and the locking section interacting therewith, in particular the pawl, jointly represent, or are part of, a latching mechanism.

In some embodiments the locking section, in particular the arch section, is not arranged with the link lever by a joint and/or is not rotatably or pivotably arranged relative to the link lever.

In several embodiments, the arch section is curved at a constant radius.

In certain embodiments, the link lever is connected to the handle in an articulated manner by only one joint.

In some embodiments, the handle of the fast-action clamping device according to the present invention comprises a first end area and a second end area. Here, the first rod recess is arranged in the first end area and the second rod recess in the second end area.

In several embodiments, the handle comprises a lever recess within which the locking section is arranged to be movable relative to the handle.

The lever recess may be a through-opening, e.g. extending from an upper side of the handle to a lower side thereof. The lever recess may be straight, at least in sections. It may extend in a curved manner at least in sections.

In some embodiments of the fast-action clamping device according to the present invention, the tension rod comprises a lever recess within which the locking section is arranged so as to be movable relative to the tension rod.

Also this lever recess may be a through-opening. The locking section may be guided or moved through it when the link lever is actuated. The lever recess of the tension rod is preferably wide enough to still have enough play, even when the locking section is passed through it, in order to be moved along its longitudinal axis itself.

In several embodiments of the fast-action clamping device according to the present invention, the locking section carries teeth and the blocking section is arranged to engage between adjacent teeth or sections of the locking section in the clamping position.

In some embodiments, the locking section is part of the link lever.

In several embodiments, the locking section is part of the handle and preferably not arranged so that it can be swung away from it.

In some embodiments, both the locking section and the blocking section are not provided jointly or each as part of the link lever or on or at it.

In several embodiments, the locking section is arranged to be only longitudinally displaceable relative to the handle (or to other structures thereof), but not pivotable.

In some embodiments, the locking section is not arranged to be movable relative to the link lever (or to other structures thereof).

In several embodiments, the fast-action clamping device comprises a mechanism for unlatching the locking section from the blocking section.

The mechanism may have a one-piece or multi-piece actuating element which is, for example, a push button or encompasses such one.

The actuating element may be arranged to be actuated using the thumb of the same hand that grasps the link lever. For this purpose, the actuating element may, for example, project beyond the handle on both sides of the handle The actuating element may be arranged so that it may be actuated from both sides of the fast-action clamping device. This may render possible the comfortable actuation of the actuating element, preferably by using one hand, for both left-handers and right-handers.

The blocking section may be mechanically coupled with the actuating element, here e.g. the push button. The actuating element, here the push button, is preferably manufactured as one piece.

The actuating element optionally comprises a preferably cylindrical section which may serve as a pressure surface for the surgeon.

This section, which is purely preferably cylindrical, may be joined with a bolt which is connected to or emerges from the section at a fixed angle.

The angle is preferably a value between 15° and 60°, more preferably between 20° and 40°, most preferably between 25° and 30°.

The bolt is, preferably with regard to the longitudinal direction of the blocking section, optionally guided in a form-fit manner within a receptacle of the blocking section.

The actuating element may be arranged so that when it is pressed, it is then moved together with the bolt, which projects at an angle from the preferably cylindrical section, in the axial direction of the preferably cylindrical section. The section is optionally defined radially, but not axially. In this, the blocking section may be shifted in the longitudinal direction of the blocking section due to the angular arrangement of the bolt and its optional form-fit reception in the longitudinal direction of the blocking section. This movement may cause the teeth of the arch section to disengage from the blocking section (or vice versa). The blocking section and the arch section are consequently in the non-clamping position.

The bolt is preferably arranged in order to be inserted in sections into a component, e.g. a sleeve-shaped component, during the movement described above.

Optionally, this component or another component comprises compression springs. They may be arranged to exert a restoring force on the actuating element, for example by exerting force on the bolt.

In addition or as an alternative to this, the blocking section is optionally connected to, or comprises, at least one spring, preferably a compression spring. This or these may for example be provided in sections in a receptacle, wherein the receptacle is designed in or at the blocking section, e.g. as a bore, opening, blind opening, etc.

The spring (or the plurality of springs) connected to the blocking section may be arranged to exert compressive force in the direction of that section of the blocking section which, in the clamping position, engages e.g. in the teeth of the arch section.

The spring connected to the blocking section may be arranged to exert compressive force (e.g. exclusively or mainly or substantially) in the longitudinal direction of the blocking section.

The spring connected to the blocking section may extend in the longitudinal direction of the blocking section by its longitudinal axis.

In this way, the spring connected to the blocking section may exert further restoring force on the blocking section, e.g. the pawl.

In some embodiments, the blocking section comprises a recess for receiving a bolt or a section thereof. The recess may be present at the edge. Alternatively, it may be designed as a through-opening with a closed circumference. The recess may serve as a guide or as a passage for the bolt. A relative movement between bolt and recess may be possible.

In several embodiments, the surgical device according to the present invention is designed as a head holding device which comprises pins for holding the head of a patient during treatment.

In some embodiments, the surgical device according to the present invention comprises a head clamp with a first arm and a second arm. Both the first arm and the second arm have hereby at least one pin each. The pins are arranged such that a patient's head may be received or clamped between them.

Furthermore, the surgical device optionally comprises a first bar and optionally a first connection arrangement for connecting the first bar to the head clamp.

The connection may be done directly, e.g. the first connection arrangement may be connected directly to a section of one of the arms, or indirectly, e.g. the first connection arrangement may itself be connected to a section of a clamp or of a clamping device connected to the arm, which may optionally also be provided.

In several embodiments of the surgical device according to the present invention, the first bar comprises, preferably at an end section thereof, a rail extending radially and/or perpendicular to the longitudinal axis of the first bar.

In some embodiments, the surgical device according to the present invention further comprises at least one bracket, and a second connection arrangement configured for connecting the bracket to the rail.

Encompassed by the present invention is also more than one bracket. The connection arrangements by which the brackets are connected to the rail may be of the same kind or different from each other.

Optionally, one or both of the arms comprises a section which respectively extends horizontally in sections and ascends therefrom in sections. The horizontal sections of the two arms may be adjustably connected to each other, for example by a ratchet or a toothed rail.

The longitudinal axis of the first bar may be the longitudinal axis of its elongated section, optionally that section which is received in the first connection arrangement.

The rail preferably extends radially in both directions, i.e. it preferably protrudes both to the left and to the right over or beyond the bar or its elongated base body.

The rail is preferably flat on its top and/or bottom surface. Elements such as screws, hooks, clamps, etc. protruding over the main plane of the top and/or of the bottom surface are preferably not provided, not part of the rail and/or not connected to the rail.

The rail is preferably longer than it is wide. It may be a plate or have a strip shape.

The rail is preferably perforated (through holes or blind holes).

Such holes or openings may comprise an internal thread.

The first bar is preferably welded to a threaded ring, which itself is welded to a threaded pin, and the latter may be welded and ground to the plate.

The rail closes the first bar preferably upwards or to one end of the bar.

The first and the second connection arrangement differ optionally from each other. In particular in the number of rotation axes, degrees of freedom, through-openings, etc.

Thus, in some embodiments according to the present invention, either the first connection arrangement or the second connection arrangement is designed to define exactly a first axis of rotation and to enable a bar or bracket received therein to rotate exclusively about the first axis of rotation by this connection arrangement (each with respect to, for example, one stationary point or section, e.g. the arm or rail, to which the connection arrangement is itself attached).

In this, the other of these two connection arrangements is designed to define at least a second axis of rotation and a third axis of rotation and to allow a bar or bracket received therein to rotate about at least both the second axis of rotation and the third axis of rotation by this connecting arrangement.

The first and the second connection arrangement optionally differ, for example in the number of axes of rotation, degrees of freedom, through-openings, etc.

In certain embodiments according to the present invention, the head holding device further comprises a second bar and also a third connection arrangement. The third connection arrangement is configured to receive the second bar together with the first bar, preferably releasably, preferably in a shiftable manner, preferably being lockable, within it. A locking mechanism such as a clamping screw or the like may be provided.

The third connection arrangement is optionally identical in construction to the first connection arrangement.

The second bar optionally has, at least in sections, the same diameter and/or the same profile as the first bar.

In some embodiments according to the present invention, the third connection arrangement is configured to define exactly one fourth axis of rotation and to enable a bar received therein to rotate exclusively about the fourth axis of rotation by this connection arrangement.

Axes of rotation may be parallel, skewed, intersecting, identical to each other.

For each of the connection arrangements mentioned herein, it may apply that the bar received by it may be fixed in several angular positions, preferably continuously, at least within a predetermined angular range of at least 45°.

In several embodiments according to the present invention, the first connection arrangement comprises a clamp or is connected thereto. The clamp serves to connect the first connection arrangement to the first arm, preferably to the section of the first arm carrying the at least one pin, e.g. to the ascending section of the arm.

In some embodiments, the clamp is designed to be releasably connectable to the arm.

In some embodiments, the clamp is designed to be shiftable along the first arm.

In several embodiments, the clamp comprises a plurality of interfaces, e.g. gear rims. These may be arranged in order to enable instruments or accessories to be coupled, preferably from more than one direction, and in their entirety preferably in more than one plane. For this purpose, they are provided, for example, at sections of the clamp which are provided at an angle to each other and/or not in the same plane.

In specific embodiments, the clamp comprises a threaded screw, but optionally not one or not exactly one claw.

In certain embodiments according to the present invention, the head holding device comprises at least one section which is made of aluminum, titanium, stainless steel, plastic, carbon, composite material, a fiber-reinforced material or a combination thereof or comprises one of the materials mentioned here.

In some embodiments, the ascending section of at least one arm does not comprise a protruding rail.

For the first and the third connecting arrangement, it may apply that it can be moved or offset along the bars or projections of the clamp inserted into it. This is done by adjusting the position of this connection arrangement relative to the bar inserted into it.

For the first connection arrangement and/or the third connection arrangement it may apply that they comprise two or exactly two through-openings into which elements to be connected to each other, such as bars, protrusions or the like, may be inserted in order to be fixed therein.

In some embodiments, any elements of the head clamping device are radiolucent.

In some embodiments, the first connection arrangement and the second connection arrangement do not define a common shifting axis of a bar received by these two connection arrangements.

In some embodiments, the first connection arrangement comprises a bar, the second does not comprise the same bar.

In some embodiments, at least one connection arrangement, optionally several, comprises two through-openings such that at least one of the bars may be received in one of the through-openings in that it may be shiftable therealong, lockable or clampable therein.

In some embodiments, at least one of the bars comprises a radially protruding pin which prevents an undesired release of the bar from a connection arrangement in at least one direction. This may depend on the rotation position of the bar within the connection arrangement.

In some embodiments, the second bar is curved in a cutting plane transverse to its cross-section.

In some embodiments, the second bar is not closed to form a ring or any other circumferential structure.

In some embodiments, the second bar comprises a circular or ring-shaped cross-section.

In some embodiments, the second bar in the second connection arrangement is not arranged rotatably relative to the latter.

In some embodiments, the second bar is at least partially hollow, in others it is not hollow in any section.

In several embodiments, the first connection arrangement comprises a locking screw or a clamping screw, the longitudinal axis of which is vertical to the longitudinal direction of the horizontal arms of the head holding device.

In several embodiments, the second connection arrangement comprises a locking screw or a clamping screw, the longitudinal axis of which is vertical to the rail and/or parallel to the longitudinal axis of the first bar.

In some embodiments, the second connection arrangement is screwed to the rail, preferably from below, e.g. by its locking screw or clamping screw.

In some embodiments, the second connection arrangement is connected to the rail in a rotation-proof manner, for example by welding, by suitable plug connections, by using an anti-rotation protection (for example in the form of radially inserted pins), or the like.

In some embodiments, the rail comprises one or several through-openings and/or one or several blind openings. Such openings may comprise threaded inserts or threaded bores.

The aforementioned openings, through-openings, bores, threaded bores, etc. may be used to attach further instruments, target devices or gel pads, for example as a hand rest, to the rail.

In some embodiments, the second connection arrangement does not extend, on a side, e.g. the one that is the upper side during use, beyond the rail. This may prevent the surgeon supporting himself on the rail from getting stuck thereon for example with his gloves or the sleeves of his surgical gown.

In some embodiments, at least any one of the connection arrangements comprises two clamping sections, which each surround a through-opening and which may be reversibly limited in diameter, preferably by only one locking screw or clamping screw, for clamping e.g. a bar. Both clamping sections may preferably be provided to be rotatable relative to each other. A gear rim, for example, can be provided between them. The rotatability relative to each other may optionally also be cancelled or allowed again using the locking screw or the clamping screw.

One or several of the above and of the following advantages may be achieved by the present invention.

An advantage of the present invention is that the surgeon has a number of degrees of freedom by using the fast-action clamping device for setting his instruments, e.g. those fixed to the head clamping device. In this, he may assume that the set position is not unintentionally lost due to the mechanism which prevents the unintentional transition to the non-clamping position. With the fast-action clamping device according to the present invention, an unintentional loosening of connections on the surgical device is advantageously avoided.

Fixing and releasing the fast-action clamping device is advantageously possible with just one hand. This enables the surgeon or medical staff to operate the device more easily and thus to "retrofit" the fixed instruments more easily.

Angular positions and the like of the instruments used in the operating field may be changed or adapted without spending much time or without even the use of tools.

A one-piece production of the arch section together with the link lever and/or with further sections of the link lever allows (as already the prevention of relative movement between the aforementioned structures by providing force-fit connections and/or form-fit connections between the aforementioned structures) advantageously to omit or avoid joints and connectors, the effort required to produce them, their vulnerability, etc.

In addition, when using a first and a second bar, he is optionally granted rotation possibilities in at least or exactly three degrees of freedom. The larger number of degrees of freedom is preferably shifted closer to the connection of the attachment comprising the bars and brackets to the arm, which may have advantages in terms of stability and strength of the structure.

Furthermore, the rail (or rails, see the following figures) mentioned herein may be of particular use to him in his work, as it allows him to support his arm, hand and the like. The head holding device according to the present invention may allow that he does not get stuck on locks, handles, screw ends and the like as described in the following embodiments.

In addition, the design of the rail and/or its connection to one of the arms of the head holding device may allow him to mount a number of brackets on the rail next to each other. These may extend in one and the same direction from the rail, e.g. into the space between the arms (e.g. instruments) or may be facing outwards (e.g. navigation; imaging, etc.). The brackets may be attached to the top and/or to the bottom of the rail, they may be rotatable and thus pivotally connected to the plate. The plate shape of some embodiments allows a broad-based support of the instrument or accessory (for example by simultaneous connection in openings of the rail that are relatively far apart from each other), which may increase the stability.

Since the rail is preferably flat and long, its dimensions may be chosen to comparatively generous, so that it offers space for coupling a large number of interfaces or instruments etc. without its weight increasing to an alarming extent.

In some embodiment, the first bar is optionally not positioned centrally under the rail. This may provide greater flexibility by rotating the first bar, sometimes turning the less protruding leg of the rail into the space between the arms and sometimes turning the more protruding leg. Should more space be needed between the attachments attached to the arms during surgery, this may allow to create said space by rotating the shorter legs of the bar (i.e. those with less projection over the first bar) into this space, but not the longer legs. A reverse handling may also be considered, should instruments have to reach further into the space. In this case, the longer leg can be pivoted into the space. Overall, the rail, if it optionally has legs of unequal length, allows a larger working area and/or working radius.

In some embodiments, target devices and/or other instruments may be attached to the rail. For this purpose, the above-mentioned openings may be used, alternatively or in addition, the rail may have one or more interfaces on at least one surface thereof (top, bottom, front, or any other), such as additional gear rims.

In several embodiments, the rail may serve as a support, for example a hand rest. A gel pad may optionally be attached.

In some embodiments, the brackets are compatible with commercially available clamps (e.g. Leyla, Greenberg systems) due to their design (e.g. a thin bracket with a round cross-section). This may advantageously save costs for the development of new clamps.

Advantageously, the first bar may be positioned at any angle to the fixed arms.

Advantageously, the attachment and/or navigation connections may be attached to the clamp. This offers considerable freedom and flexibility when attaching additional instruments.

The connection arrangement allows advantageously to attach a plurality of additional instruments and navigation connections.

Advantageously, the rail is secured against accidental falling out.

The attachment (bar with rail, with or without bracket, possibly with clamp) may advantageously be easily released from the respective arm using the proposed clamp connections, in particular by releasing only one main clamp (see reference number 201 in the figures), advantageously without a tool.

The present invention is exemplarily described below based on the accompanying, partly simplified figures, in which identical reference numerals refer to the same or to similar components. The following applies in the figures.

Figure 1:
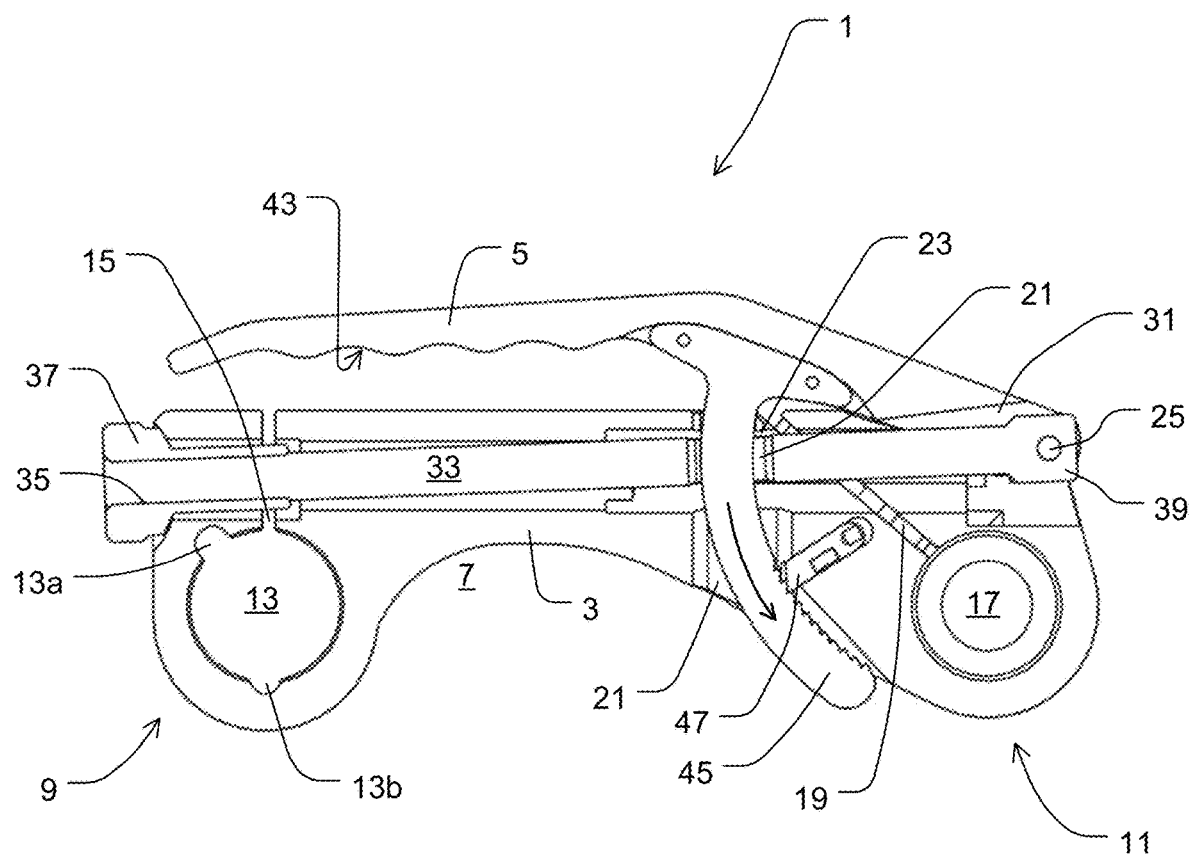
FIG. 1 shows an exemplary embodiment of a device according to the present invention cut parallel to the drawing plane with a handle and a link lever from the side, wherein the link lever is in a clamping position.

FIG. 1 shows an exemplary embodiment of a device 1 according to the present invention with a handle 3 and a link lever 5 in a closed arrangement of the device 1, i.e., in the arrangement in which the device 1 would have a clamping effect when used as intended.

The elongated handle 3 has a middle part, on which a recessed grip 7 is optionally designed. At the ends of the middle part of the handle 3 there is a first end area 9 and a second end area 11, which are thickened with respect to the middle part.

A first rod recess 13 and a first clamping gap 15 or a second rod recess 17 and a second clamping gap 19 are respectively introduced into the end areas 9, 11.

Objects to be connected, such as, for example, a connecting rod of a surgical head holder and of attachments to an operating table (75, 77, see FIG. 6), which are not shown in FIG. 1, are insertable into the rod recesses 13, 17, which are preferably round in cross-section, wherein when the clamping gaps 15, 19 which extend from the inside of the rod recesses 13, 17 towards an outside of the handle 3 narrow, the objects are clampable in a manner explained in more detail below.

The first rod recess 13 and/or the second rod recess 17 may optionally comprise anti-rotation protections which prevent the objects clamped to them from twisting unintentionally around their longitudinal axis or at least make it more difficult for them. Such anti-rotation protections are designed, using the example of the first rod recess 13, exemplarily as (in this example two) grooves 13a, 13b. Corresponding spring sections (e.g. in the sense of springs of spring-groove connections) or projections of the objects to be clamped may be inserted into them.

Other forms or shapes of recesses than the grooves 13a, 13b shown here, as well as any forms of projections are also considered or contemplated.

In the second end area 11 or between the second end area 11 and the middle part or in another site, a lever recess 21 is optionally provided, which is open on a cover side 23 of the handle 3 lying opposite the recessed grip 7. The lever recess 21 may be a through-opening.

Furthermore, link pins or hinging devices 25, preferably having a circular cross-section, are provided in the second end area 11 in transverse direction of handle 3. They hold the link lever 5 on the handle 3 rotatably relative to the handle 3.

The link lever 5 comprises a recess 31 into which an end section of a tension rod 33 is inserted as an actuation rod and is rotatably connected to the link lever 5.

The tension rod 33, which is designed with a rounded cross-section over the major part of its length, comprises a preferably thread section 35 at an abutment end, onto which an abutment screw 37, optionally with a thickened abutment screw head, may preferably be screwed from the abutment side of the handle 3. This abutment screw 37 may be used to adjust or set how much the first clamping gap 15 and/or the second clamping gap 19 is to be narrowed or made smaller by the rotatable link lever 5. If, for example, the rods to be e.g. braced, are already arranged very closely, i.e. without play, in the first rod recess 13 and/or in the second rod recess 17, the respective clamping gap can only be marginally reduced by the link lever 5. It is advantageous if the abutment screw 37 can be adjusted accordingly in this case.

At a mounting end 39 opposite the abutment end, the tension rod 33 is optionally designed with a rectangular cross-section, wherein a rod axle recess 41 extending in the transverse direction (see FIG. 4) is incorporated in the tension rod 33 in the end area of the mounting end 39. With e.g. a bearing pin, the tension rod 33 is rotatably connected to the link lever 5 in the pre-assembled state.

With the help of an optional eccentric, which is visible or outlined at the recess 31, or another suitable design, the tension rod 33 can be braced, in use, by pivoting the link lever 5 in order to clamp the rods to be exemplarily fixed in the rod recesses 13, 19.

An actuating section 43 of the link lever 5 adjacent to the mounting end 39 is optionally angled in an ergonomic manner and is preferably at least as long as the middle part of the handle 3.

An arch section 45 may extend through the lever recess 21 and moveable relative thereto. The arch section 45 may be provided in one-piece or integral with the link lever 5 and/or with no possibility of relative movement between the arch section 45 and the link lever 5, or alternatively it may be connected to the latter e.g. by joining methods such as screwing, welding, etc.

The arch section 45 may have teeth which, should the arch section 45 be bent as shown in FIG. 1, may lie on its inside.

A pawl 47 may be provided in the handle 3, in particular in its second end area 11. This may be shiftable, preferably along one or along only one straight line. It may be arranged to engage, e.g. with a front/end section thereof, into the teeth of the arch section 45.

Figure 2:
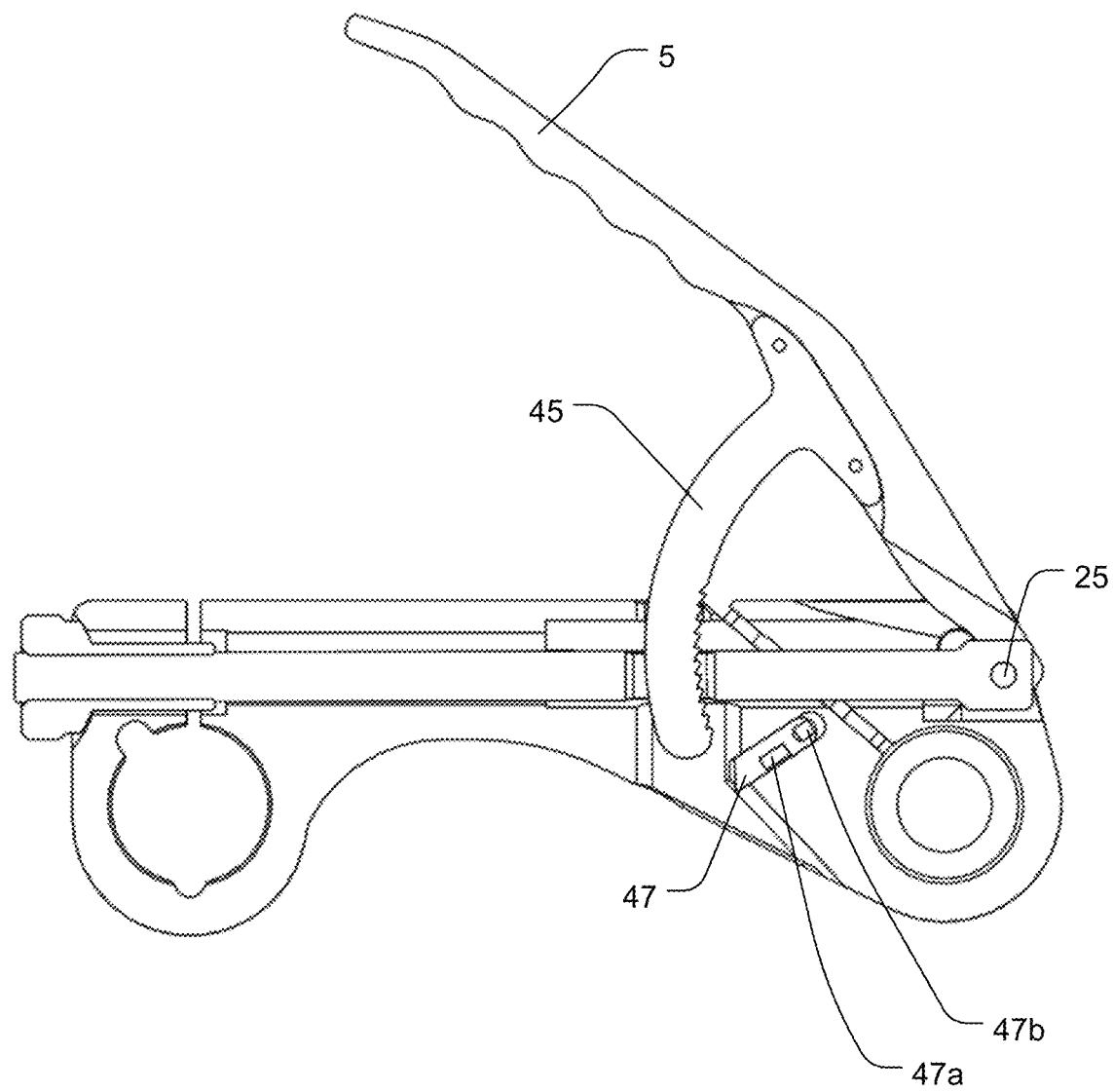
FIG. 2 shows the device of FIG. 1 according to the present invention, wherein the link lever is in a non-clamping position.

The arrangement of the teeth of the arch section 45 and the pawl 47 is preferably such that the arch section 45 can be moved in one direction along the pawl 47 (in FIG. 1 in the direction of the arrow), but not also against this direction. In this way the arch section 45 is prevented from moving out of the lever recess 21 (upwards in FIG. 1) by the pawl 47 engaging between its teeth. It can only move further in (downwards in FIG. 1). Due to this design, the arch section 45 may be held in lever recess 21, which is why the link lever 5 connected to it can be pressed further against the handle 3, but cannot be swiveled away from handle 3 easily or even unintentionally in order to change from the clamping position of link lever 5 shown in FIG. 1 to a non-clamping position as shown in FIG. 2.

The pawl 47 in the embodiment shown here may have a recess 47a for receiving a bolt, e.g. the bolt 59 shown in FIG. 10 and explained with reference to FIG. 10. As shown in FIG. 2, the recess 47a may be marginal. Alternatively, it may be designed as a through-opening with a closed circumference.

In the embodiment shown here, the pawl 47 may further optionally comprise at least one opening 47b for receiving, for example, a compression spring 67a. Its exemplary mounting position and function is described in detail regarding FIG. 12 and FIG. 13.

A mechanism for unlocking or disengaging the pawl 47 such that it no longer engages the teeth of the arch section 45, but allows a transition from the clamping position to the non-clamping position, is also provided and is described below with reference to FIG. 3 and further with reference to FIGS. 10 to 13.

Figure 5:
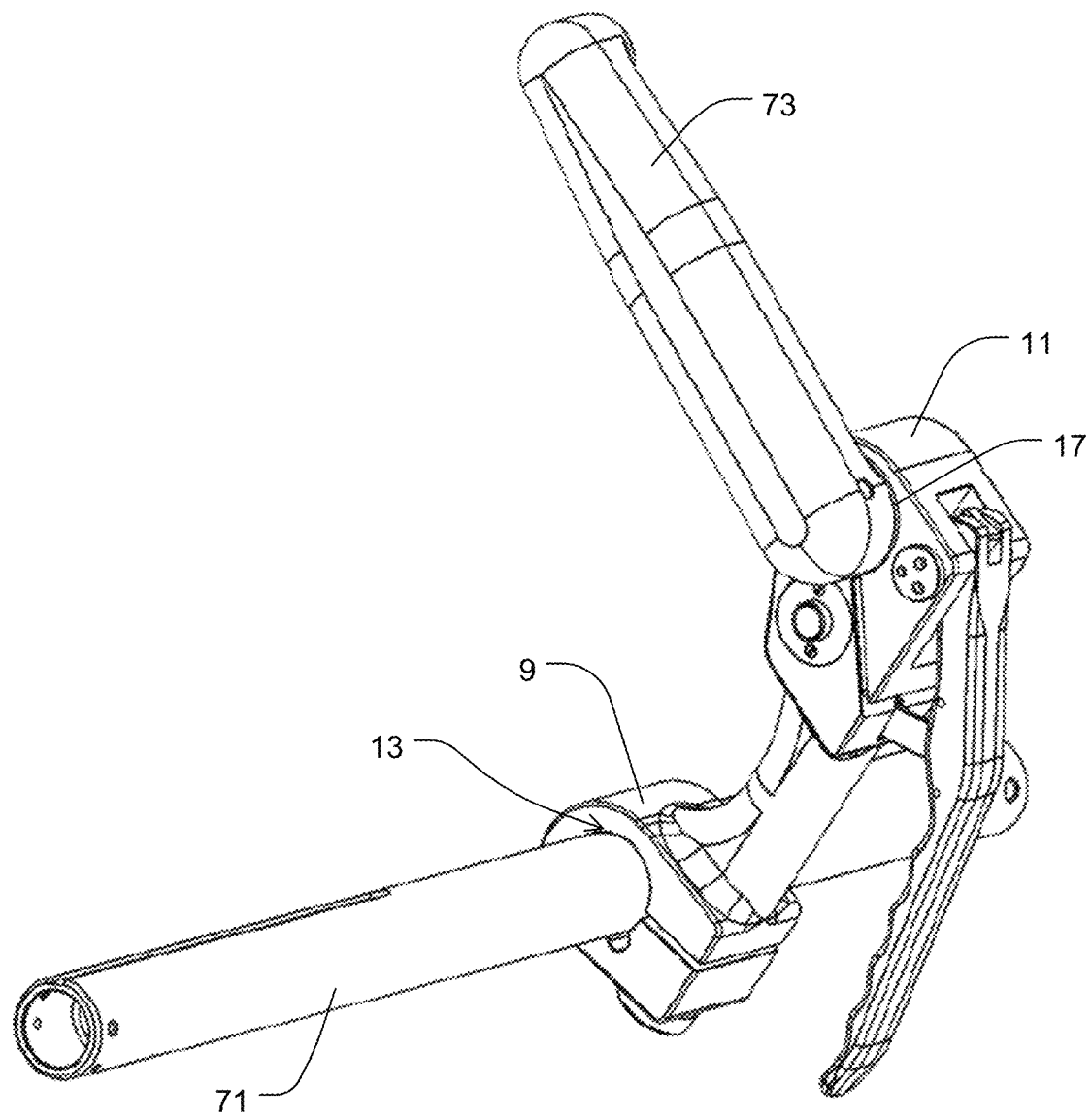
FIG. 5 shows the device of the preceding figures during use.

In the non-clamping position, it is possible, for example, to insert the rod 71 shown in FIG. 5 or the arm 73 also shown there into the first rod recess 13 or the second rod recess 17 or to move it therein. The non-clamping position may therefore also be referred to as the insertion position.

FIG. 2 shows the device of FIG. 1 according to the present invention, with the link lever 5 in the non-clamping position. It can be seen that the pawl 47 no longer engages in the teeth of the arch section 45, which is why the arch section 45 can move completely or partially out of lever recess 21 against the direction shown in FIG. 1 and the free end of the link lever 5 may pivot around the hinging device 25 away from the handle 3.

Figure 3:
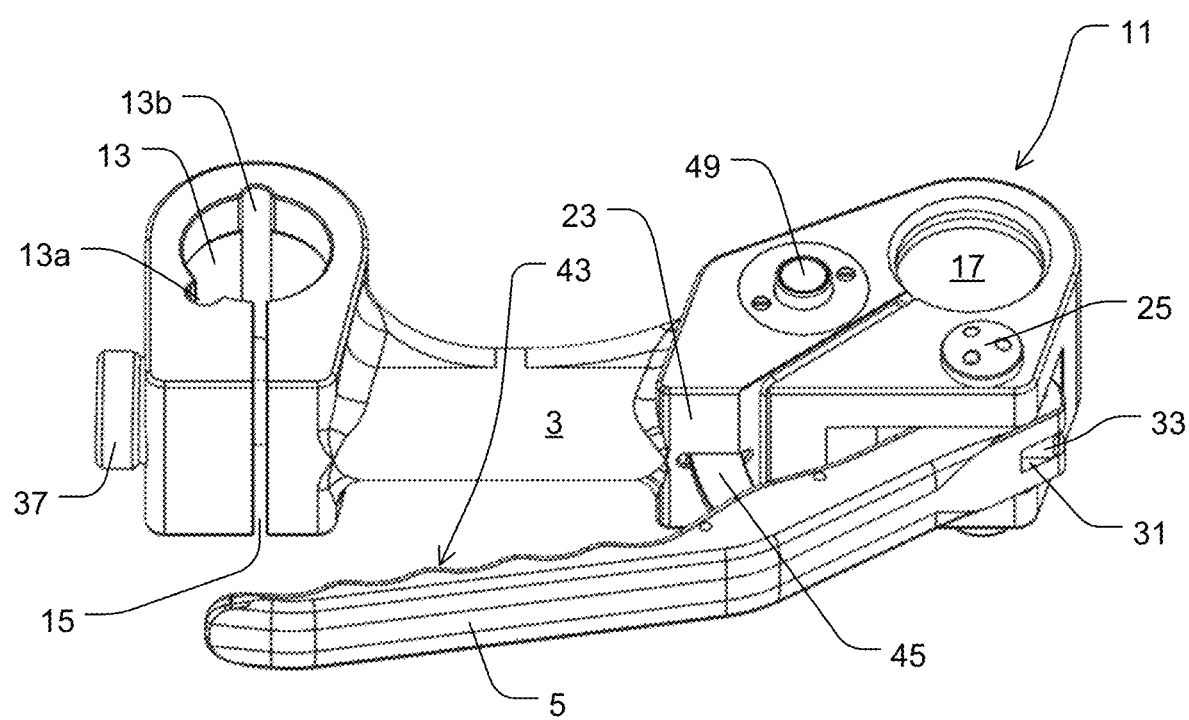
FIG. 3 shows the device of FIG. 1 and FIG. 2 obliquely from above, but unlike in FIG. 1 or FIG. 2 not being cut.

FIG. 3 shows the device of FIG. 1 and FIG. 2 obliquely from above, but unlike in FIG. 1 or FIG. 2 not being cut. The link lever 5 is in turn in a non-clamping position.

A push button 49 can be seen, which is optionally part of the mechanism for unlocking the pawl 47. If it is pressed, the pawl 47 withdraws from the row of teeth of the arc section 45 and no longer prevents the latter from withdrawing completely or partially from the lever recess 21.

Instead of a push button 49 or other parts of the mechanism for unlocking shown here by way of example, any other suitable mechanism can be provided which prevents an unwanted transition from the clamped position to the non-clamped position, but enables an intentional transition.

The mechanism which is to be actuated for unlocking may be automatically engaged by a return mechanism such as a spring, so that, optionally without the need of applying for instance pressure onto the push button 49 or on any other section, the locking section such as here the pawl 47 engages with the locking section such as here the row of teeth of the arch section 45.

Figure 4:
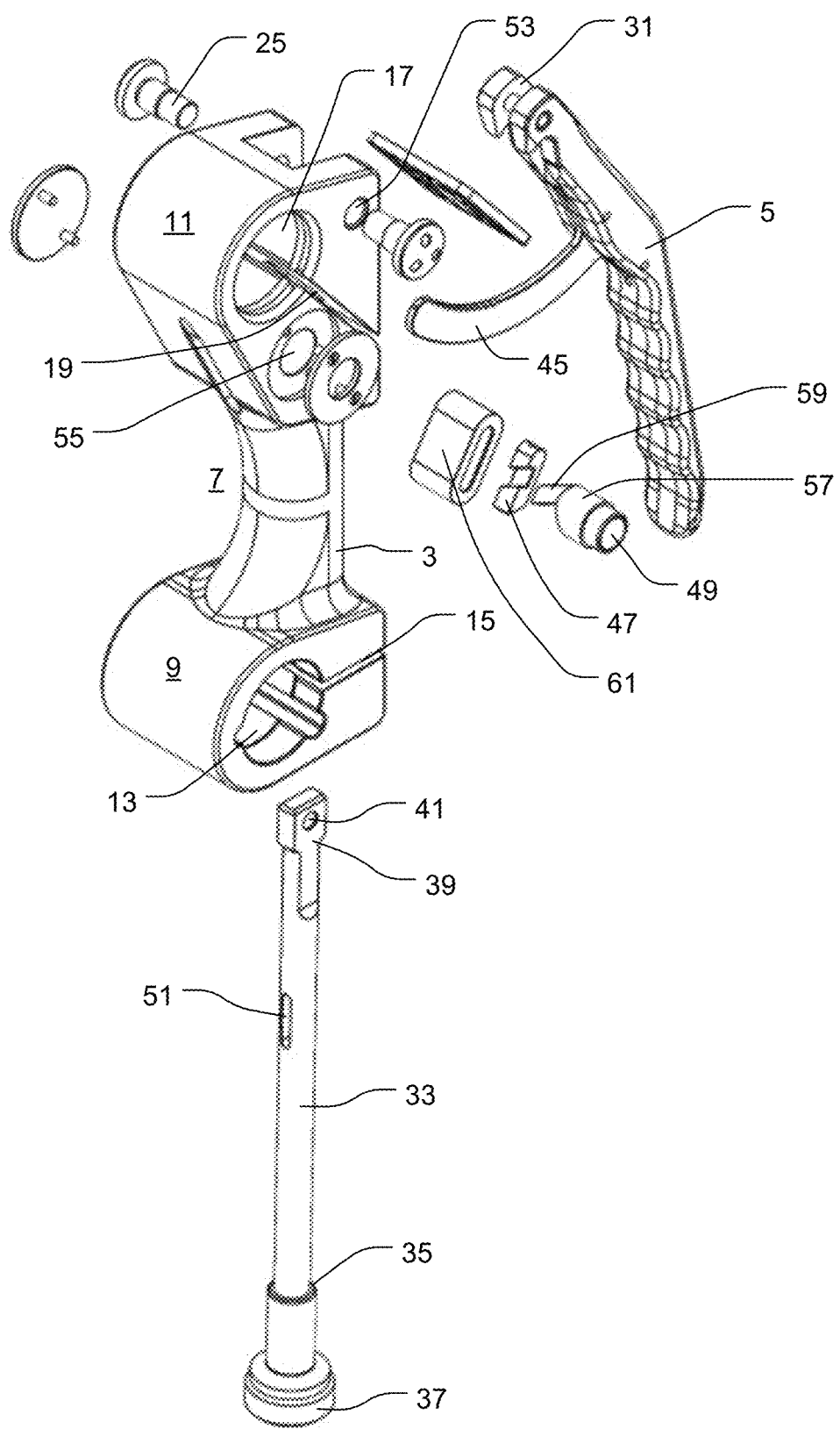
FIG. 4 shows the device of the preceding figures in an exploded view.

FIG. 4 shows the device of the preceding figures in an exploded representation.

It can be seen that the tension rod 33 in this exemplary embodiment comprises a through-opening 51, through which the arch section 45 is passed when the device 1 of the arch section 25 is in use, in order for it to move therein during the transition from the clamping position to the non-clamping position.

As can be further seen, the mounting end 39 may have a rectangular cross-section or at least two parallel surfaces, while other sections of the tension rod 33 may have a round cross-section.

In addition to the second rod recess 17 and an optional through-opening 53 for receiving the hinging device 25, the second end area 11 may optionally comprise a further through-opening 55, which serves to receive part of the mechanism, comprising the push button 49, for preventing an unintentional transition from the clamping position to the non-clamping position.

The second rod recess 17, the through-opening 53 and the further through-opening 55 may comprise parallel axes, i.e. they can be parallel to each other.

The hinging device 25 may be provided to hold the link lever 5 rotatably in the handle 3. It may also be provided to hold the mounting end 39 of the tension rod 33 rotatably in the recess 31 of FIG. 1 of the link lever 5.

The reference numerals 57, 59 and 61 are described with reference to FIG. 10.

FIG. 5 shows the device 1 of the preceding figures during use. The device 1 is shown in the clamping position in which it simultaneously clamps a rod 71 in the first rod recess 13 and an arm 73 in the second rod recess 17.

Rod 71 and arm 73 may be part of a device for holding a head holding device 1000 on an operating table.

Figure 6:
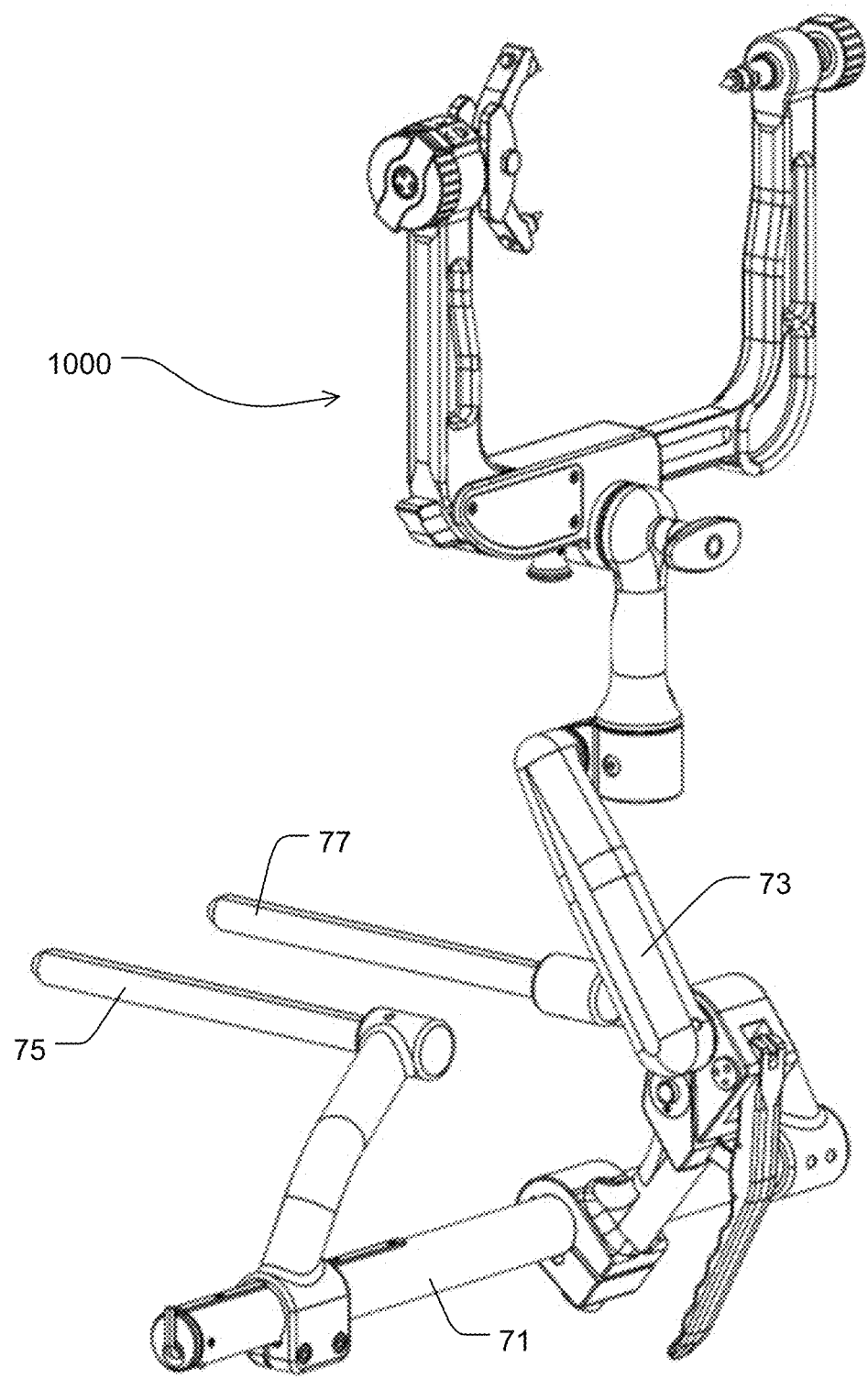
FIG. 6 shows the device of the preceding figures as part of a head holding device.

FIG. 6 shows the device 1 of the preceding figures, in particular of FIG. 5. In its use as shown here, it connects a device according to the present invention, here a head holding device 1000, to insertions 75, 77, by which the head holding device 1000 may be held on an operating table.

Figure 7:
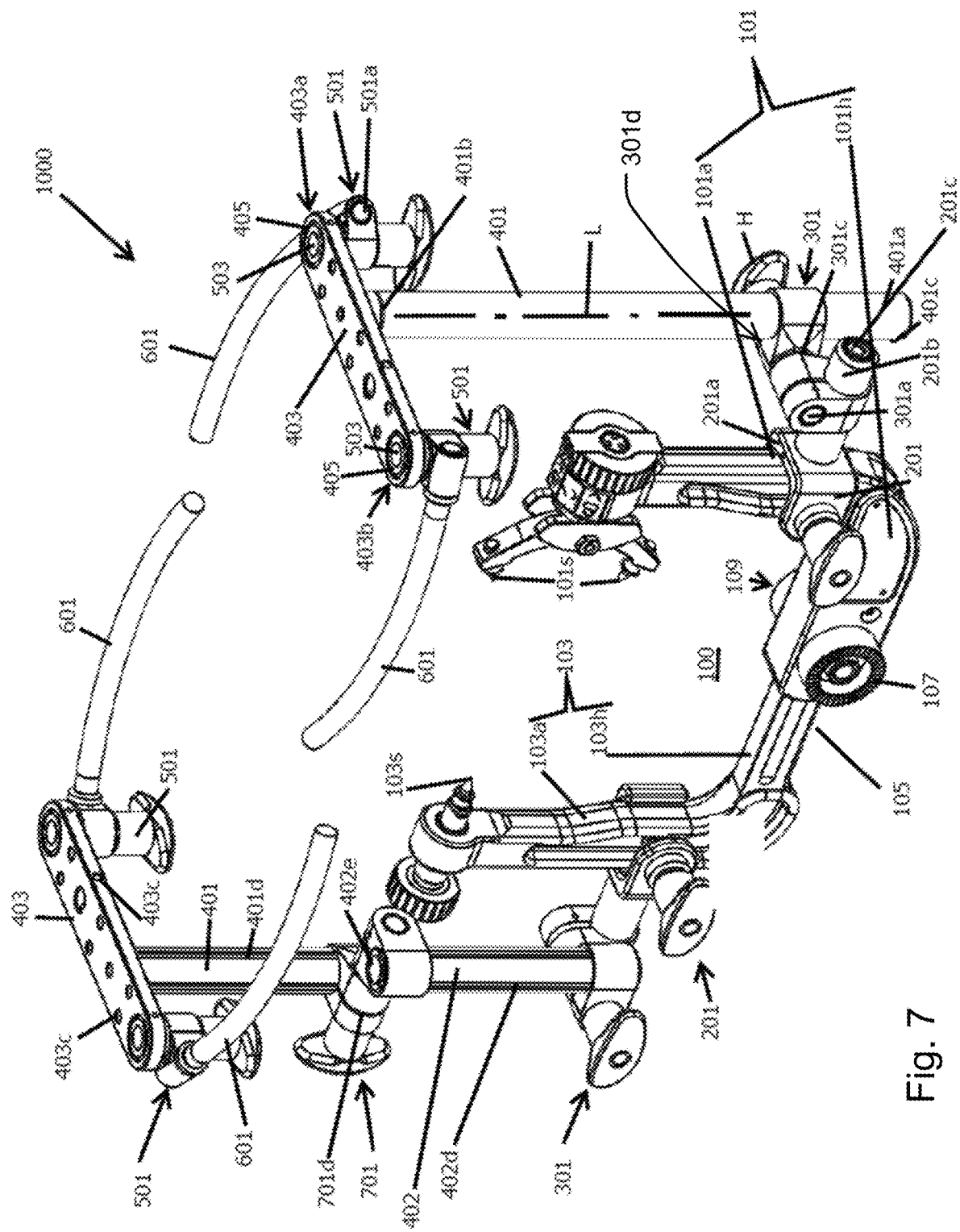
FIG. 7 shows a surgical device according to the present invention in an exemplary embodiment in a perspective view from the top right.

FIG. 7 shows a surgical device, here exemplarily designed as surgical head holding device 1000, in slight perspective from above.

The head holding device 1000 has a head clamp 100 with a first arm 101 and a second arm 103.

The first arm 101 comprises a horizontal section 101h (with respect to its arrangement in FIG. 7) and a section 101a ascending therefrom.

Likewise, the second arm 103 comprises a horizontal section 103*h* (with respect to its arrangement in FIG. 7) and a section 103*a* ascending therefrom.

The ascending section 101*a*, 103*a* may alternatively be described as "protruding" or "standing away".

The horizontal sections 101*h* and 103*h* may be connected to each other in a non-releasable or releasable manner. In each of these cases, they may be connected relative to one another in order to be adjustable relative to each other. Thus, as in the example in FIG. 7, a toothed rail 105, a ratchet, or the like may be provided.

One, two or more gear rims 107, 109 may be provided for attaching accessories or instruments to the head clamp 100, e.g. on one of the horizontal sections, as shown here for the horizontal section 101*h*. Other interfaces or docking points for attaching accessories or instruments to the head clamp 100 may be provided, for example, at horizontal sections 101*h* and 103*h* or ascending sections 101*a* and 103*a*. They may for this purpose be provided integrally or connected (screwed, welded, etc.).

Both the first arm 101 and the second arm 103 each carry, using their ascending sections 101*a* and 103*a*, at least one pin for clamping the skull between them, wherein the ascending section 101*a* here exemplarily carries two pins 101*s* and the ascending section 103*a* carries one pin 103*s*.

The first arm 101 is connected to a clamp 201 in its ascending section 101*a*.

The clamp 201 may optionally be provided to be displaced along the ascending section 101*a*. The range in which a displacement is possible may optionally be limited, for example by webs, steps, the choice of the diameter or another dimension of the arm 101 at this point, etc.

The clamp 201 may comprise a clamping shoe 201*a* and a protrusion 201*b* being optionally connected thereto in a rotation-proof manner or integral therewith. In FIG. 7 the protrusion 201*b* is exemplarily designed as a cylindrical section.

The projection 201*b* or another section of the clamp 201 may comprise an interface or coupling point for connecting an instrument or accessory, e.g. in the form of a gear rim 201*c*.

A first connection arrangement 301, which in this example comprises three through-openings, of which, optionally exactly, two comprise a variable inner diameter, is releasably clamped in one of these through-openings on projection 201*b*. As long as it is not clamped, the first connection arrangement 301 is rotatable around the protrusion 201*b*. Tightening a clamping screw 301*a*, e.g. by a screw handle or handle H, clamps the first connection arrangement 301 with the protrusion 201*b* or against it.

A first bar 401 is inserted into a further through-opening with a variable diameter of the first connection arrangement 301. It may also be rotated within the through-opening receiving it and/or may be displaced in its height in relation to the first connection arrangement 301 as long as the clamping screw 301*a* has not been tightened or this has not been prevented in some other way.

As shown in FIG. 7, the first connection arrangement 301 thus defines a first axis of rotation, which in relation to FIG. 7 corresponds to the longitudinal axis of the protrusion 201*b*, and a second longitudinal axis which corresponds to the longitudinal axis L of the first bar 401 being shown in dash-dotted line.

A third axis of rotation, which is defined by the first connection arrangement 301, is made possible by a twisting arrangement, which is here optionally designed as a combination of two gear rims 301*c*, as may optionally also be present on other connection arrangements shown in FIG. 7. It corresponds in FIG. 7 to the longitudinal axis of the clamping screw 301*a*, or is parallel to it.

The first bar 401 comprises a first end section 401*a* (bottom of FIG. 7) and a second end section 401*b* (top of FIG. 7).

The first end section 401*a* is here exemplarily a free end, which optionally carries a radially protruding locking pin 401*c*.

The locking pin 401*c* may ensure that the first bar 401, which is rotatable within the first connection arrangement 301 in the unclamped state, can only be pulled out of the through-opening of the first connection arrangement 301 at a small angle of rotation along its longitudinal direction, since the locking pin 401*c* can only be passed through the through-opening together with the first bar 401 in the area of a clamp opening 301*d*.

Locking pins similar to locking pin 401*c* may optionally be provided on any of the rods described herein.

The first bar 401 comprises a rail 403. Here, it is optionally connected to the second end section 401*b* or manufactured integrally therewith.

The rail 403 can be welded to the first bar 401, integrally manufactured or otherwise connected in a rotationally fixed, non-releasable and/or form-fit and/or force-fit manner. If, as in the present example, the possibility of rotation between bar 401 and rail 403 is dispensed with, a mechanism for allowing and preventing rotation may also be dispensed with, which may have the advantage that protrusions and instabilities that would be caused by such a mechanism do not have to be provided nor occur at this prominent location where the surgeon works.

The rail 403 can form a T-shape with the first bar 401. The rail 403 may have two opposite ends 403*a* and 403*b*, at which the rail 403 ends freely.

The rail 403 may have openings 403*c* or through-openings 405 for fastening additional devices or instruments. These may be provided on and/or accessible from any surface of the rail 403.

For manufacturing and cost reasons, the rail 403 may have a straight course, optionally not a curved course. If the rail 403 has a curved or otherwise non-straight course, it is advantageously convex to the head, i.e. its ends are farther from a center of the head clamp 100 than a central section of the rail 403. The straight course, like the course of the rail 403 curved or angled away from the center, allows the largest possible free space between rods in which the surgeon can find space for surgery.

The rail 403 has coupling points to which accessories or instruments can be attached directly or indirectly.

These coupling points include through-openings 405, which may be provided at one or both ends 403*a* and 403*b*, and which, e.g. may be equipped with a thread.

A second connection arrangement 501 is connected to the latter at the left end of the rail 403, here, exemplarily, by its left through-opening 405. A similar or identical connection arrangement 501 is connected to the right end of the rail 403, here exemplarily by its right through-opening 405.

The second connection arrangements 501 in turn have a clamping screw which may be tightened and released again by a handle. Other locking mechanisms which do not effect by a screw connection, but use e.g. toggle levers, eccentrics or similar, are also being considered.

The second connection arrangement 501 comprises an insertion opening 501*a* into which a bracket 601 is inserted. The bracket may be pivoted by the second connection arrangement 501 in one plane, in the settings of FIG. 7 exemplarily in the horizontal plane. The axis of rotation about which this pivoting takes place is defined by the second connection arrangement 501 and corresponds in the example of FIG. 7 to the longitudinal axis of the clamping screw, the free end 503 of which more or less ends or closes with the upper surface of the rail 403.

In the embodiment shown in FIG. 7, the second connection arrangement 501 allows the bracket 601 to be rotated about exactly one axis of rotation, namely the one discussed above.

For this purpose, the bracket 601 can be inserted into the second connection arrangement 501 in a rotation-proof or form-fit manner.

The bracket 601 may in turn be used to attach instruments, hooks, spreaders or the like. Its profile may be circular, ring-shaped or of a different shape.

FIG. 7 shows an optional further connection arrangement 501 of the above-mentioned type, which is also connected to the above-mentioned rail 403.

The above description of FIG. 7 has been limited to structures or additions which are connected to the first arm 101 or are supported by the latter.

Descriptions of elements that are connected to the first arm 101 apply analogously also to the same or to similar elements that are connected to the second arm 103, which can be seen not least from the figures. In order to avoid repetitions, their description is omitted. Instead, reference is made to the description of such elements with reference to the first arm 101.

The following description of FIG. 7 deals with structures or attachments which are connected to the second arm 103 or are supported on the latter. In this, hereinafter, those elements that differ from elements that are described in connection with the first arm 101 will be discussed.

The second arm 103 with its ascending section 103a is connected also to a clamp 201, as already discussed above. A first connection arrangement 301, as already also discussed above, is connected to the clamp 201.

In the first connection arrangement 301 there is a second bar 402 optionally comprising a spring 402d which prevents the second bar 402 from rotating in the first connection arrangement 301. It is pointed out, however, that this spring 402d is optional as well as other anti-rotation mechanisms (non-round cross-section, etc.) and that the first bar 401 could also comprise such a spring.

A groove which together with the spring 402d forms an anti-rotation protection for the second bar 402 in the first connection arrangement 301, may be provided in the first connection arrangement 301. Alternatively, the spring may be provided in the first connection arrangement 301, but the groove may be provided on the second bar 402. Also alternatively, another anti-rotation protection may be provided instead of a spring-groove system. However, any kind of anti-rotation protection is always optional.

As FIG. 7 shows, the second bar 402 with a further end section thereof, which optionally carries at the front end an interface, e.g. a gear rim 402e, is inserted in a further connection arrangement 701, herein referred to as the third connection arrangement. The third connection arrangement 701 may be designed like the second connection arrangement 501.

The third connection arrangement 701 connects the second bar 402 to a further first bar 401. Like the second bar 402, the first bar 401 may optionally comprise an anti-rotation protection, for example, in the form of a spring 401d, a groove, or the like.

Just like the first bar 401 which is described with reference to the first arm 101, here too the first bar 401 may be connected to a rail 403, as described above, or may be manufactured integrally.

The first connection arrangement 301, which is connected to the second arm 103 as well as to the second bar 402 by the clamp 201, preferably allows or defines a rotation around exactly two axes of rotation.

The third connection arrangement 701, to which the second bar 402 is also connected, preferably allows or defines a rotation about exactly one axis of rotation.

Figure 8:
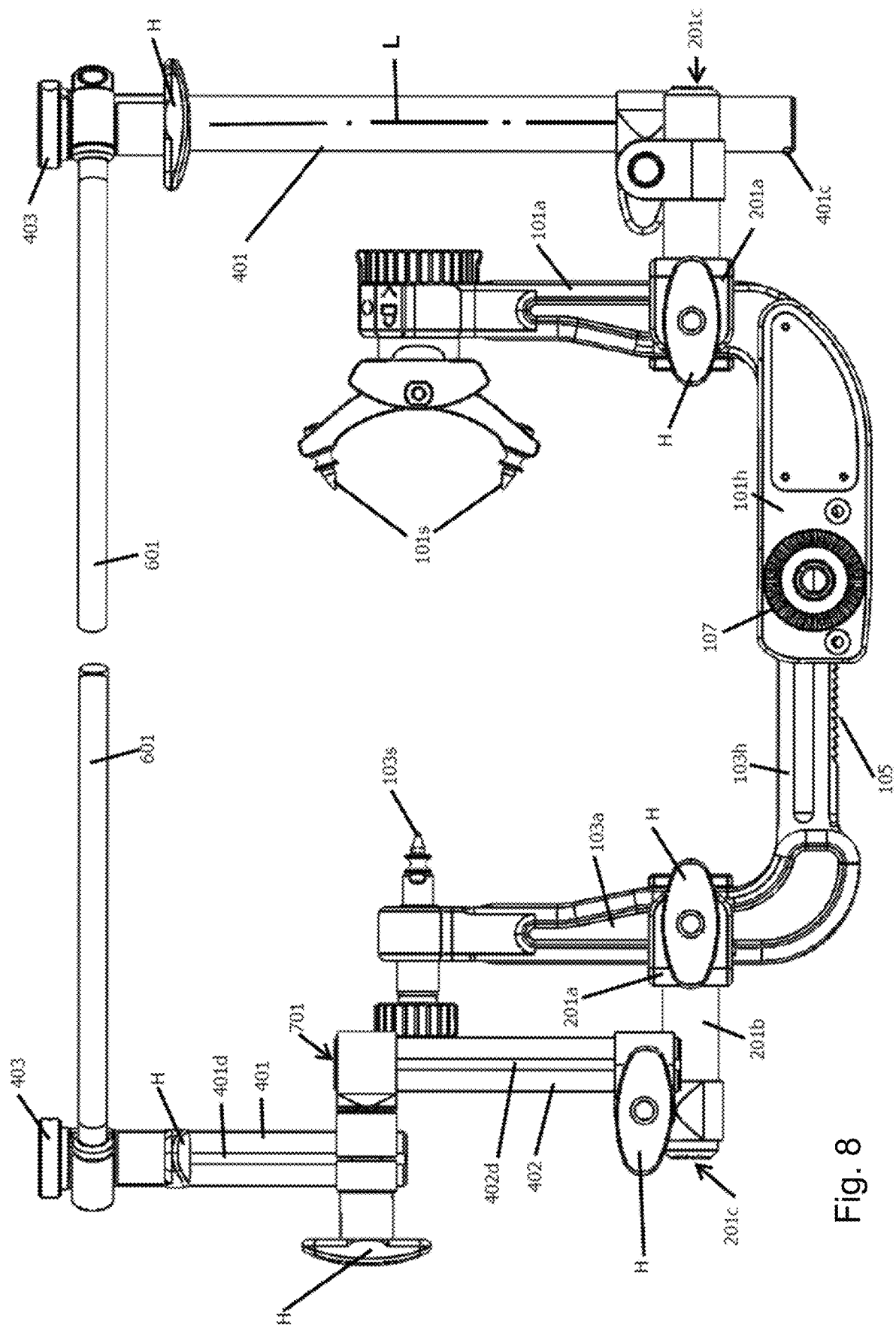
FIG. 8 shows sections of the surgical device of FIG. 7 in a side view.

FIG. 8 shows the surgical head holding device 1000 of FIG. 7 from the side.

Handles used to tighten or lock clamping screws are marked with the reference sign H in FIG. 8.

Figure 9:
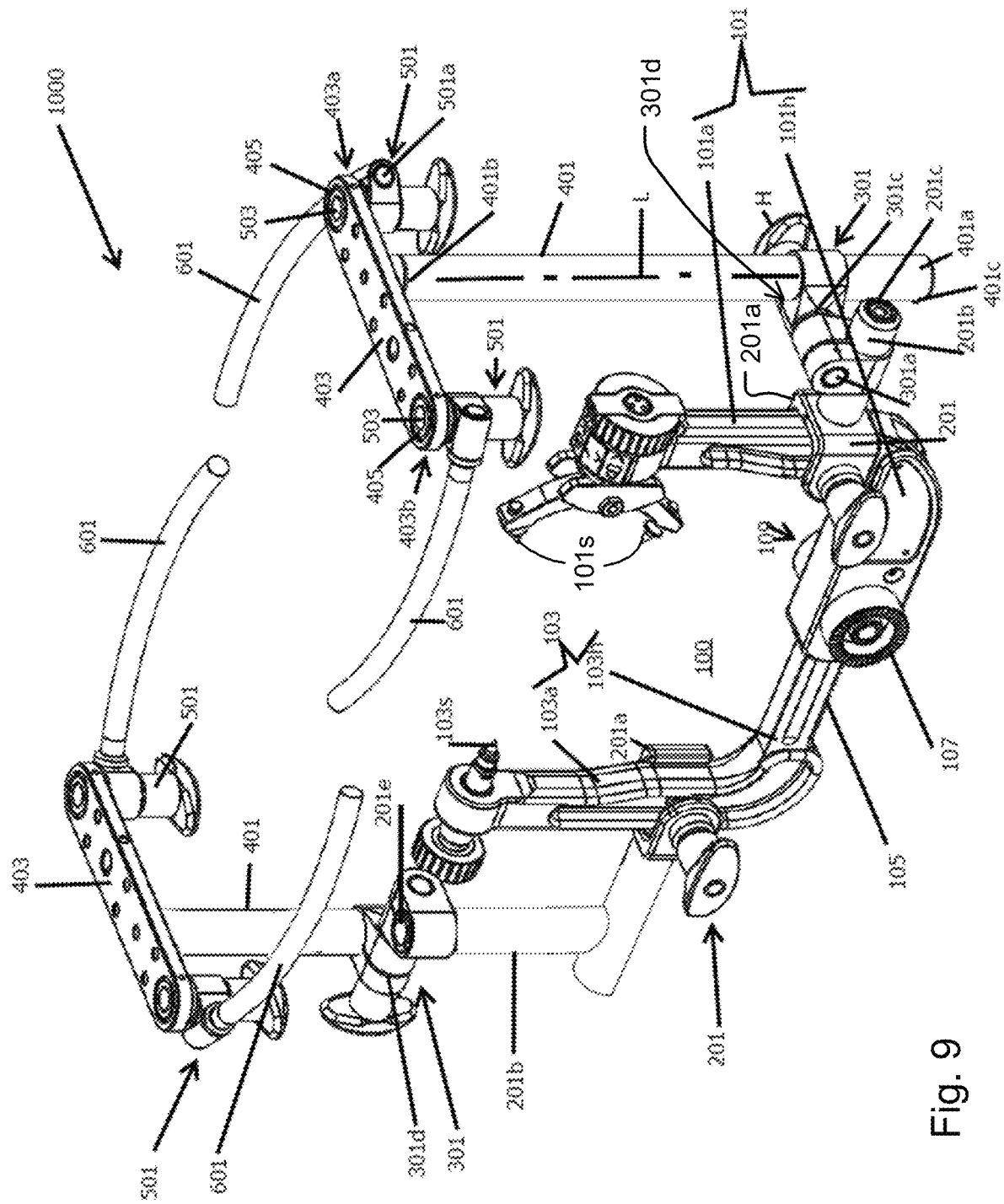
FIG. 9 shows a surgical device according to the present invention in an exemplary second embodiment in a perspective view from the top right.

FIG. 9 shows a surgical head holding device 1000 according to the present invention in an exemplary second embodiment in a perspective view from the top right.

This embodiment corresponds essentially to that of FIG. 7. Only the differences from the embodiment of FIG. 7 are to be mentioned below. They only relate to the structure that is supported on the second arm 103.

Starting from a clamping shoe 201a of the clamp 201, as is also known from FIG. 7, the protrusion 201b extends in a form-fit manner. Unlike the protrusion 201b in FIG. 1, however, this is not designed as a straight section, but has both a horizontal section (in relation to FIG. 9) and a section ascending from it, which, in FIG. 9, runs vertically. The section referred to herein as horizontal and the section referred to herein as ascending may be perpendicular to each other, they may be at a different angle to each other, but they are not parallel and do not have a common longitudinal axis.

A joint may be provided between the horizontal section and the ascending section. Preferred, however, there is no joint. The horizontal section and the ascending section are optionally made in one piece or integrally. Alternatively, they are welded together.

The first connection arrangement 301 in turn connects the protrusion 201b to the first bar 401 in a manner known from FIG. 7 and also shown in FIG. 9 for the first arm 101.

A gear rim 201e or another interface may optionally be arranged on the clamp 201 on the end face or at an upper end thereof, for example for coupling further accessories, such as further holders, positioning devices and/or instruments, etc.

A groove-spring connection or other anti-rotation protection on the first bar 401 may be provided, but is not required or it is dispensable.

A pin lock on the first bar 401 for protection against unwanted pulling out or release may be provided, but is not shown in FIG. 9. Such a securing against pulling out, which may be designed as a pin lock, may be optionally provided here as well as on any other rod mentioned herein.

Figure 10:
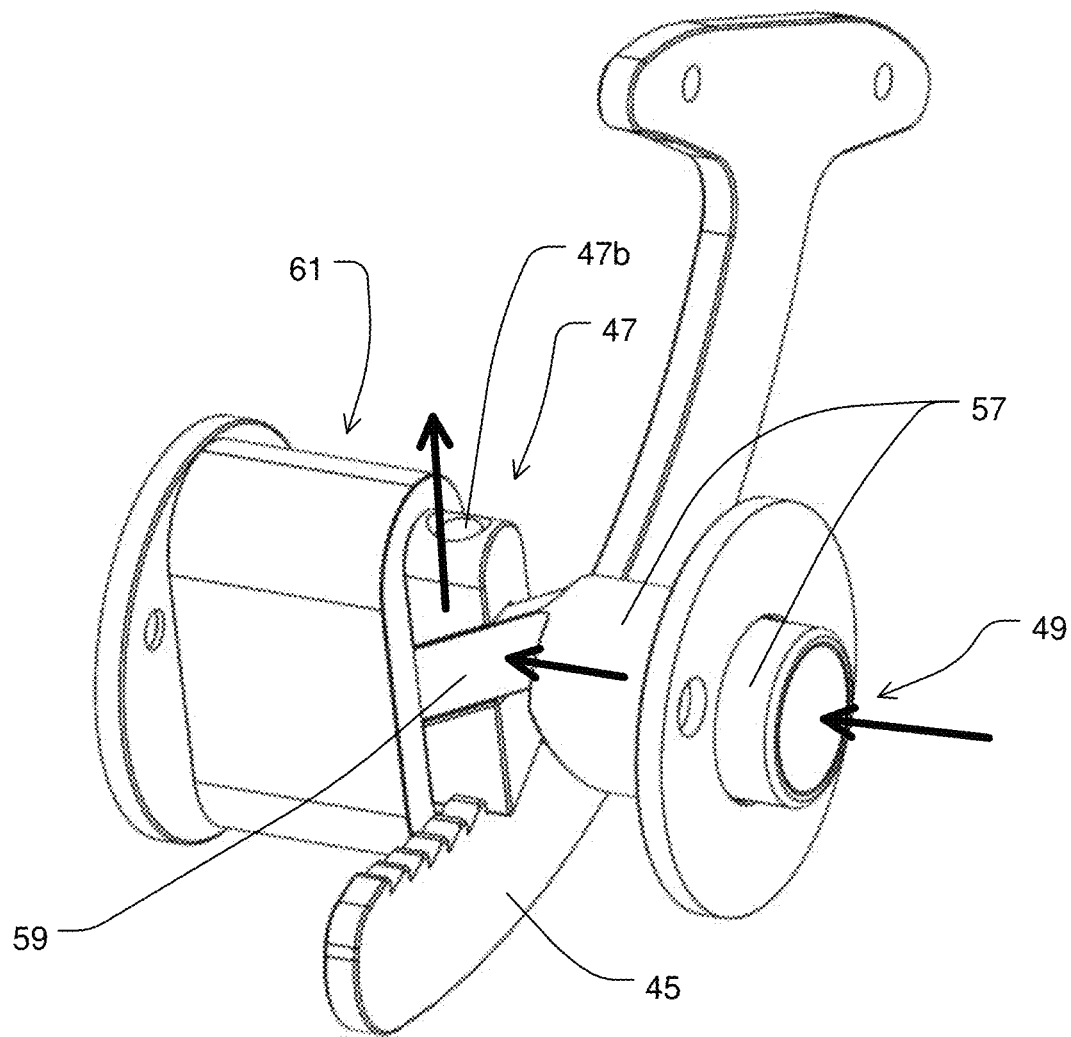
FIG. 10 shows a perspective view of an assembled state of the components involved in fixing the pawl on the arch section by a push button.

FIG. 10 shows the components involved in locking the optional pawl 47, as exemplarily shown in the exemplary embodiment of FIG. 1, on the arch section 45 by the push button 49. FIG. 10 shows the arrangement of these components in their interconnected or assembled state in a perspective view.

The push button 49 optionally comprises a preferably cylindrical section 57, which may comprise a recess at the front/end side for its simplified manual insertion.

A bolt 59 may be connected to the cylindrical section 57, which is connected in an angular position to the section 57 or at a fixed angle α thereto. The push button 49 is exemplarily manufactured in one-piece. The angle is or assumes—e.g. in a side view, e.g. as shown in FIG.

11—preferably between 15° and 60°, particularly preferably between 20° and 40°, most preferably between 25° and 30°.

Figure 11:
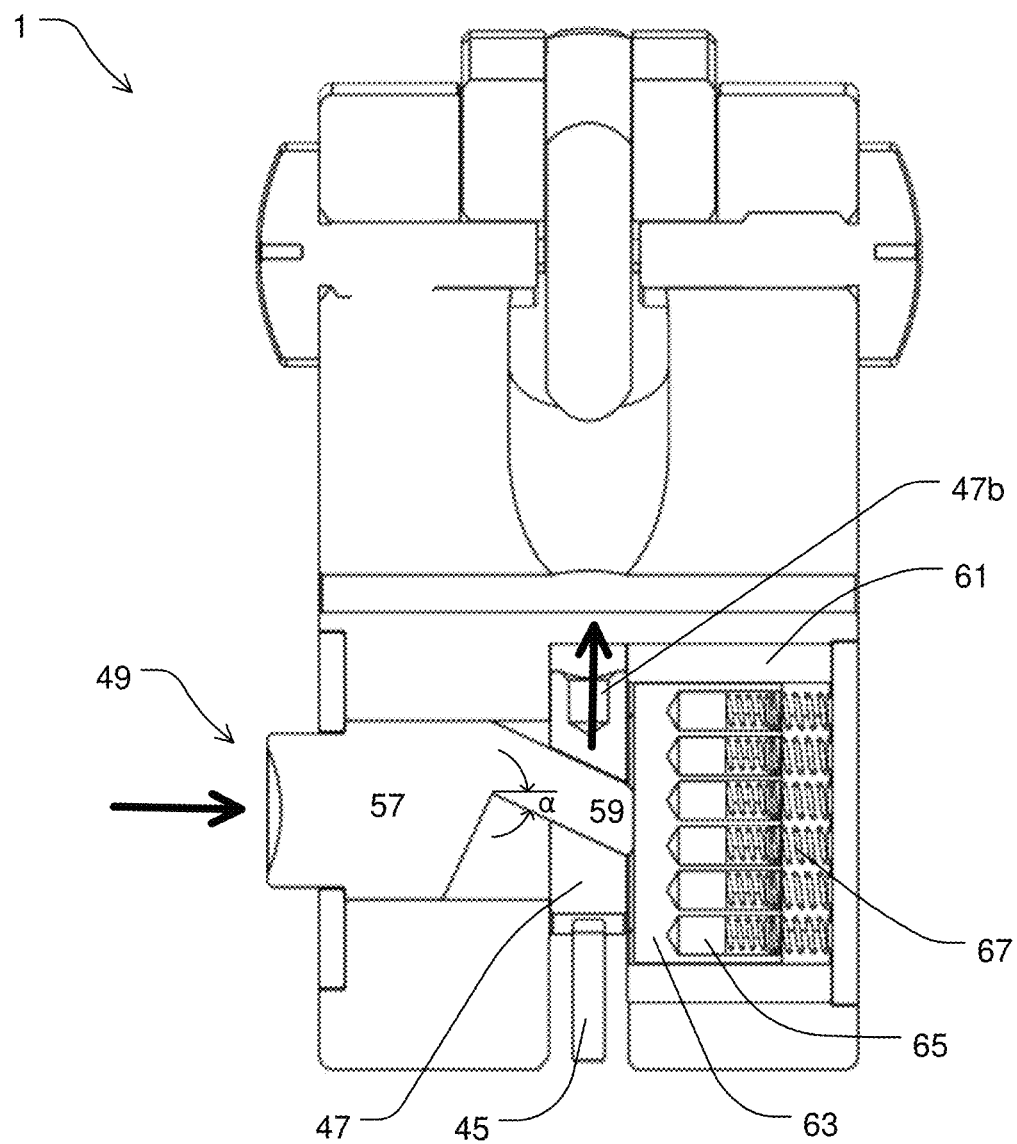
FIG. 11 shows in a cross-section of FIG. 3 the push button without link lever.

The angle α may result or may be established or formed between an outer surface of the section 57, from which the bolt 59 extends, and one or more outer surfaces of the bolt 59, as exemplarily shown in FIG. 11 for both the upper side of the bolt 59 and the underside thereof.

As far as the longitudinal direction of the pawl 47 is concerned (in FIG. 10 this corresponds to the up-down direction), the bolt 59 is guided in a form-fit manner in the recess 47a of the pawl 47.

If the push button 49, which may consist of, for example, section 57 and bolt 59, is pressed in the direction of the arrow, i.e. in FIG. 10 (see also FIG. 11) in the axial direction of section 57, the bolt 59 projecting at an angle from section 57 is also moved in the axial direction. Since the section 57 is fixed radially, but not axially, as can be seen in FIG. 11, the pawl 47 is shifted upward in the direction of the arrow due to the angular arrangement of the bolt 59 and its form-fit reception in the pawl 47 in/along the longitudinal direction of the pawl 47. As a result of this movement, the teeth of arch section 45 no longer engage in the pawl 47 and arch section 45 is then in the non-clamping position. The arch section 45 is optionally freely movable in the non-clamping position in both directions along the curved longitudinal axis of the arch section 45. The link lever 5 (see FIG. 1), which is optionally connected to the arch section 45, can be opened or folded upwards in order to move or shift exemplarily clamped rods in the first 13 and/or second 17 rod recess (see FIG. 1).

The angled bolt 59 is partially inserted into a, e.g. sleeve-shaped, component 61 during the movement described above. Purely exemplarily, compressing springs 67 are arranged in it, which exert a restoring force on the push button 49, for example by exerting force on the bolt 59. The spring force of the exemplary compression springs causes the push button 49 to be pushed back into the starting position shown in FIG. 10, in which the pawl 47 again engages in the teeth of the arch section 45. This starting position corresponds to the clamping position. The arrangement of the exemplary compression springs 67 in the sleeve-shaped component 61 is described in more detail in FIGS. 11 to 13.

FIG. 11 shows a section of the representation in FIG. 3 in a sectional plane which shows the push button 49, but not the link lever 5.

The push button 49 comprises the cylindrical section 57 and the angled bolt 59. The bolt 59 comprises an angle α of approximately 30 degrees to the horizontal purely by way of example. If the angle is less than 30 degrees, the force required to press in the push button 49 and thus to unlock the arch section 45 is advantageously smaller, but the displacement path is longer. Conversely, at an angle greater than 30 degrees, the force required to press in the push button 49 becomes greater, but the displacement path is advantageously shorter.

The front/end face of the angled bolt 59 rests on an insert 63 with a plurality of blind holes 65. Compression springs 67 are exemplarily introduced into the blind holes 65. When the push button 49 is pressed in the direction of the arrow, the insert 63 is displaced by the abutting front/end face of the bolt 59 and the compression springs 67 are pressed together. At the same time, the pawl 47 is pressed upward in the direction of the arrow and the arch section 45 is unlocked. In this position the arch section 45 may be moved in both directions along its longitudinal axis or longitudinal extension. As long as the push button 49 is pressed, the compressed compression springs exert a restoring force on the push button 49. This means that without actively pressing the push button 49, the pawl 47 is returned to the clamping position.

In the following FIG. 12 and FIG. 13 the lower half of FIG. 11 is shown in an actively pressed-in state of the push button 49 (FIG. 12) and in a non-pressed in state (FIG. 13), i.e. in an unloaded initial state. The component 61 is not shown for reasons of clarity.

Figure 12:
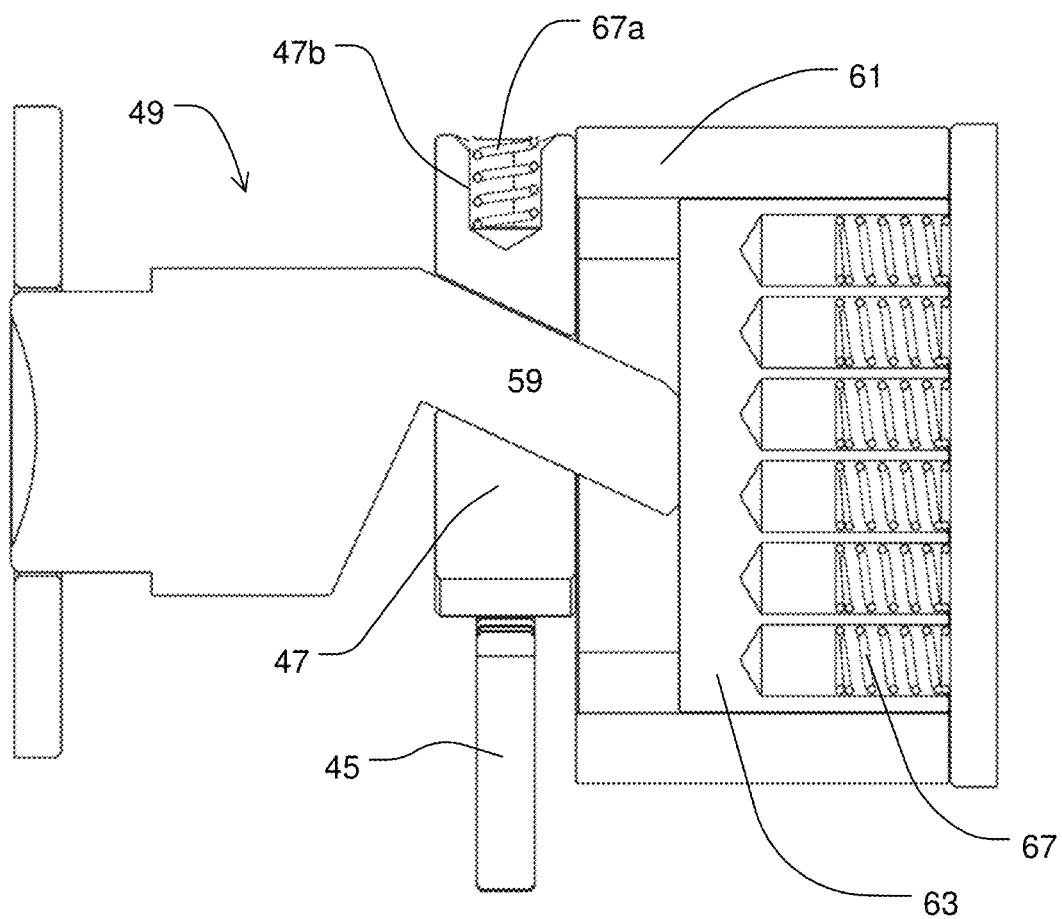
FIG. 12 shows a section of FIG. 11 with a pushed push button in a non-clamping position of the pawl.

FIG. 12 shows a section from FIG. 11 with the push button 49 pressed down in the non-clamping position of the pawl 47. The teeth of the arch section 45 are visible and the pawl 47 is actively moved upwards by the angled bolt 59. The exemplary compression springs 67 (at least one such spring, preferably a compression spring, is optionally provided here) are in the compressed state, i.e. a restoring force is exerted on the push button 49.

In addition, the compressive force of the optional compression spring 67a, which can be received at least in sections in the opening 47b (which is designed, for example, in the form of a bore or an opening, a blind hole or the like), acts as a further restoring force on the pawl 47. Hence, this provides additional securing of the clamping position, i.e. the position of the pawl 47 shown in FIG. 13, which is engaged in the teeth of the arch section 45.

In FIG. 12 the optional compression spring 67a is shown in compressed state and thus actively exerts a downward compressive force in relation to the representation in FIG. 12.

This optional compression spring 67a may also act advantageously as an additional securing of the clamping position in order to securely close the locking mechanism for achieving or maintaining the clamping position, e.g. even if the other compression springs 67 should no longer exert the required compression force, a mechanical failure occurs, e.g. due to material fatigue, or another impairment is present.

Figure 13:
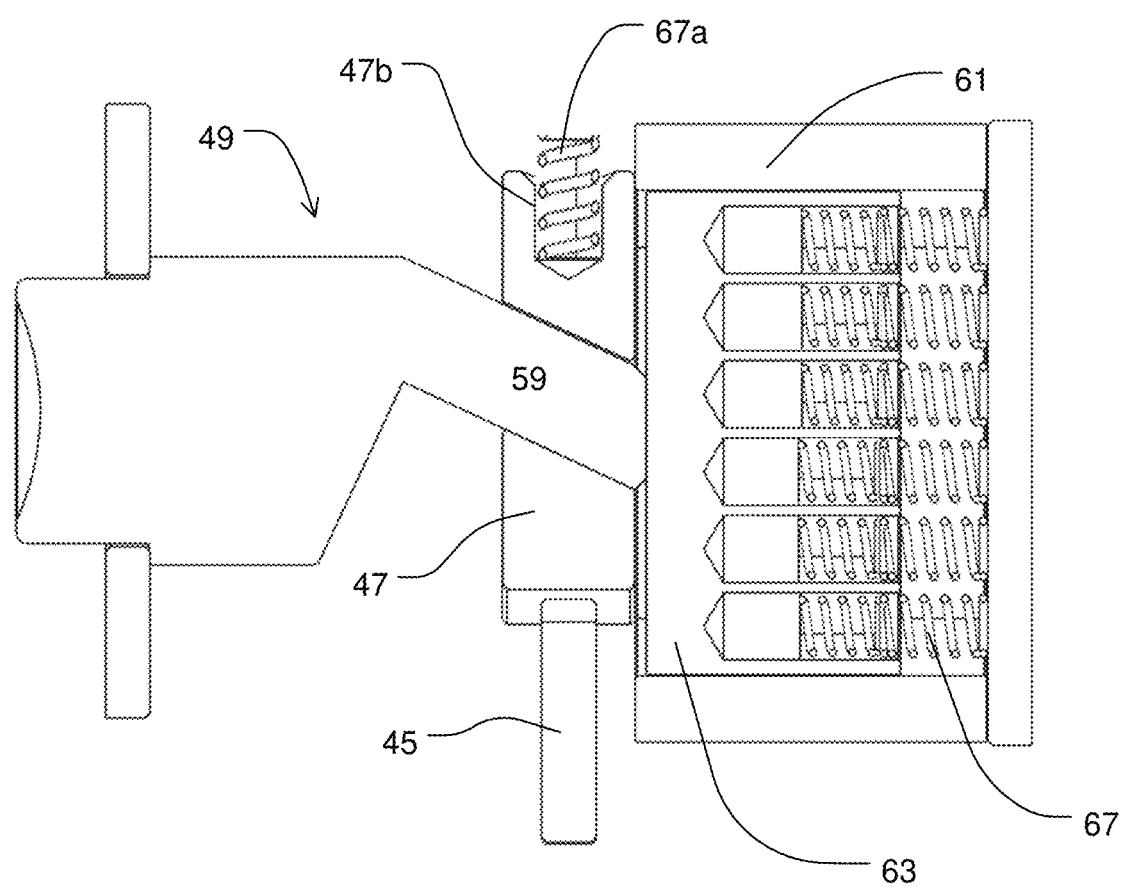
FIG. 13 shows a section of FIG. 11 with a non-pushed push button in the clamping position of the pawl.

FIG. 13 shows a section from FIG. 11 with the non-pressed push button 49 in the clamping position of the pawl 47. The teeth of the arch section 45 are not visible and the pawl 47 is not shifted by the angled bolt 59. The exemplary compression springs 67 are in the relaxed state, i.e. no restoring force is exerted on the push button 49.

In FIG. 13, the optional compression spring 67a is shown in the relaxed or non-compressed state and thus does not exert any compressive force on the pawl 47.

LIST OF REFERENCE NUMERALS 1 device
3 handle
5 link lever
7 recessed grip
9 first end area
11 second end area
13 first rod recess
13a groove
13b groove
15 first clamping gap
17 second rod recess
19 second clamping gap
21 lever recess
23 cover side
25 hinge or hinge mechanism
31 recess
33 tension rod
35 threaded section
37 counter bearing screw 39 mounting or fastening end
41 rod axle recess
43 actuating section
45 arch section
47 pawl
47a recess
47b opening or passage or hole or reception
49 push button
51 through-opening
53 through-opening
55 through-opening
57 section, or cylindrical section of the push button
59 angled bolt of the push button
61 sleeve-shaped component
63 insert
65 blind hole
67, 67a compression spring
71 rod
73 arm
75 insertion, arm or extension
77 insertion, arm or extension
1000 head holding device
100 head clamp
101 first arm
101h horizontal section of the first arm 101
101a ascending section of the first arm 101
101s pin
103 second arm
103h horizontal section of the second arm 103
103a ascending section of the second arm 103
103s pin
105 toothed rail
107 gear rim
109 gear rim
201 clamp
201a clamp shoe
201b protrusion
201c gear rim
201e gear rim
301 first connection arrangement
301a clamping screw
301c combination of two gear rims
301d clamp opening
401 first bar
401a end section
401b end section
401c locking pin
401d spring
402 second bar
402d spring
402e gear rim
403 rail
403a end
403b end
403c openings
405 through-opening
501 second connection arrangement
501a insertion opening
503 free end of the clamping screw
601 bracket
701 third connection arrangement
H screw handle, handle
L longitudinal axis of the first post
α angle

The invention claimed is:
1. A fast-action clamping device, comprising
a handle;
at least a first rod recess and/or a second rod recess, each for receiving a section of an object, and for clamping the section within the rod recess by transferring the fast-action clamping device from at least one non-clamping position into at least one clamping position;
a tension rod arranged to apply tension to the first rod recess and/or to the second rod recess for effecting the clamping by transferring the fast-action clamping device from the non-clamping position into the clamping position;
a link lever which is pivotally connected to the handle by a hinging mechanism and which is connected directly or indirectly to the tension rod such that when the link lever is pivoted, the tension applied by the tension rod on the first rod recess and/or on the second rod recess is changed;
wherein the link lever comprises, or is connected to, a locking section formed as an arch section comprising a plurality of teeth, which is arranged to prevent, together with a blocking section comprising a pawl, interacting with the locking section by the pawl engaging the teeth, an automatic transition of the link lever from a position of the link lever set by a user in the direction of the non-clamping position, the blocking section, the at least first rod recess and second rod recess and the tension rod each being part of, or comprised by, the handle.

2. The fast-action clamping device according to claim 1, wherein the fast-action clamping device comprises the first rod recess and the second rod recess,
wherein the handle comprises a first end area and a second end area, wherein the first rod recess is arranged in the first end area, and wherein the second rod recess is arranged in the second end area.

3. The fast-action clamping device according to claim 1, wherein the handle comprises a lever recess within which the locking section is arranged to be movable relative to the handle.

4. The fast-action clamping device according to claim 1, wherein the tension rod comprises a lever recess within which the locking section is arranged to be movable relative to the tension rod.

5. The fast-action clamping device according to claim 1, comprising a mechanism with an actuating element for unlocking the locking section from the blocking section.

6. The fast-action clamping device according to claim 5, wherein the actuating element is a push button, for unlocking the locking section from the blocking section.

7. A surgical device for use in a medical treatment, wherein the surgical device comprises at least one fast-action clamping device according to claim 1.

8. The surgical device according to claim 7, designed as a head holding device which comprises pins for holding the skull of a patient during a treatment.

9. The surgical device according to claim 8, comprising:
a head clamp having a first arm and a second arm, wherein both the first arm and the second arm have each at least one pin for receiving or clamping the skull therebetween;
a first bar;
a first connection arrangement for connecting the first bar to the head clamp.

10. The surgical device according to claim 8, wherein:
the first bar comprises, a rail extending radially and/or perpendicularly to the longitudinal axis of the first bar.

11. The surgical device according to claim 10, wherein:
the rail that extends radially and/or perpendicularly to the longitudinal axis of the first bar is at an end section of the first bar.

12. The surgical device according to claim 8, further comprising:
a bracket;
a second connection arrangement configured to connect the bracket to the rail.

\* \* \* \* \*